US00PP28160P3

(12) United States Plant Patent
McCoy, Jr.

(10) Patent No.: US PP28,160 P3
(45) Date of Patent: Jul. 4, 2017

(54) ***CYNODON DACTYLON* PLANT NAMED 'CD08'**

(50) Latin Name: *Cynodon dactylon*
Varietal Denomination: CD08

(71) Applicant: Samuel Robert McCoy, Jr., Awendaw, SC (US)

(72) Inventor: Samuel Robert McCoy, Jr., Awendaw, SC (US)

( * ) Notice: Subject to any disclaimer, the term of this patent is extended or adjusted under 35 U.S.C. 154(b) by 0 days.

(21) Appl. No.: 14/999,441

(22) Filed: May 5, 2016

(65) Prior Publication Data

US 2016/0338249 P1 Nov. 17, 2016

Related U.S. Application Data

(60) Provisional application No. 62/161,942, filed on May 15, 2015.

(51) Int. Cl.
*A01H 5/12* (2006.01)

(52) U.S. Cl.
USPC ..... Plt./389

(58) Field of Classification Search
USPC ..... Plt./389
See application file for complete search history.

*Primary Examiner* — Annette Para

(57) ABSTRACT

A new and distinct cultivar of *Cynodon dactylon* plant named 'CD08', characterized by its dark green leaf color, medium leaf blade width, dense foliage canopy, low seed head production, vigorous growth habit and the uniformity and stability of these characteristics from generation to generation.

3 Drawing Sheets

Latin name of the genus and species: The Latin name of the novel variety disclosed herein is *Cynodon dactylon.*

Variety denomination: The inventive variety of *Cynodon dactylon* disclosed herein has been given the variety denomination 'CD08'.

BACKGROUND OF THE INVENTION

The present invention relates to a new and distinct vigorous-growing perennial variety of *Cynodon dactylon*, which has been given the variety denomination of 'CD08'. Its market class is PLT/389. 'CD08' is intended for use as a lawn grass in gardening, landscaping, sports fields and amenity horticulture.

Parentage: The new *Cynodon dactylon* cultivar is a chance seedling selection discovered in a cultivated planting of openly pollinated *Cynodon dactylon* 'WGP3' (not patented in the United States, Australian Plant Breeder's Rights application number 2008/111), at a wholesale plant nursery in Awendaw, S.C. In March 2008 a single seedling selection was discovered growing among a group of 'WPG3' plants grown in 4 inch nursery pots. Said seedling exhibited a denser foliage canopy which the inventor attributed to freely-branching stolons, shorter stolon internodes, and a slightly broader leaf texture when compared to the parent plant. Stolons of the seedling were harvested and replanted for further evaluation to confirm the characteristics initially observed.

Asexual reproduction: The new variety 'CD08' was first asexually propagated by cutting and division of stolons in 2008 at a wholesale plant nursery in Awendaw, S.C. 'CD08' has since been further asexually propagated by means of cutting and division of stolons through at least 5 generations and the distinctive characteristics of the variety have remained stable and true to type through successive cycles of asexual propagation.

SUMMARY OF THE INVENTION

The following characteristics of the new cultivar have been repeatedly observed and can be used to distinguish 'CD08' as a new and distinct cultivar of *Cynodon dactylon* plant:

1. Dark green leaf color; and
2. Medium leaf blade width; and
3. Dense foliage canopy; and
4. Freely-branched stolons; and
5. Short stolon internodes; and
6. Vigorous stolon growth; and
7. Vigorous rhizome and root growth and
8. Low occurrence of inflorescences.

BRIEF DESCRIPTION OF THE DRAWINGS

The accompanying photographs show, as nearly true as it is reasonably possible to make the same in color illustrations of this type, typical foliage and growth characteristics of the new cultivar. Colors in the photographs differ slightly from the color values cited in the detailed description, which accurately describes the colors of 'CD08'.

DETAILED BOTANICAL DESCRIPTION

Figure 1:
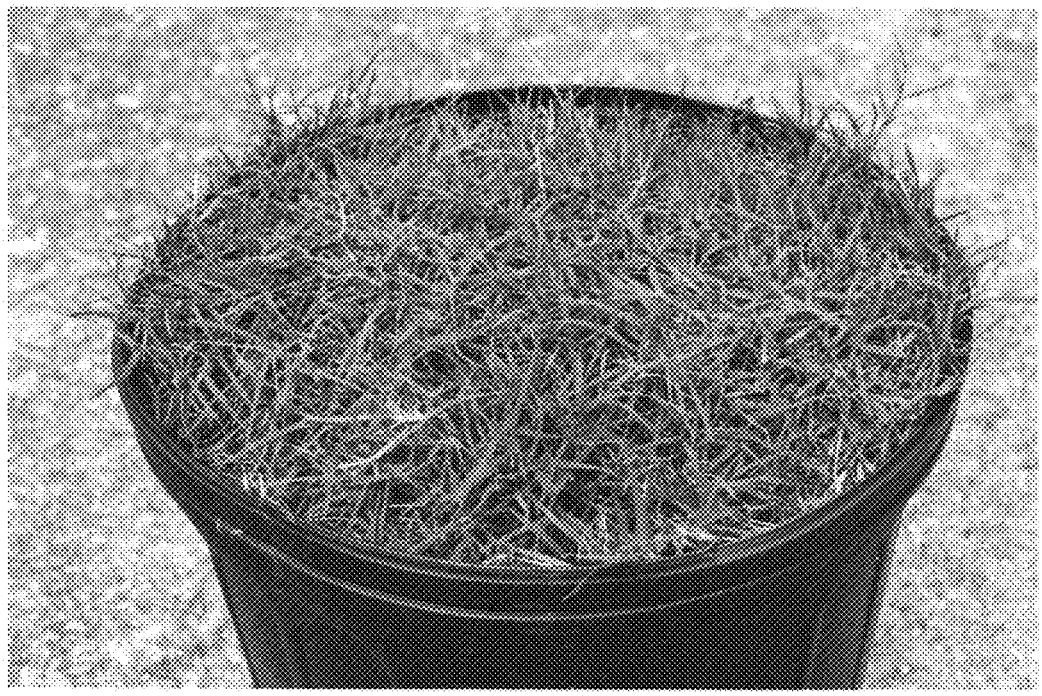
FIG. 1 shows a 'CD08' plant in a 3-gallon nursery pot, grown for approximately 10 months in an outdoor environment showing plant growth 4 weeks after pruning in spring in Awendaw, S.C.
Figure 2:
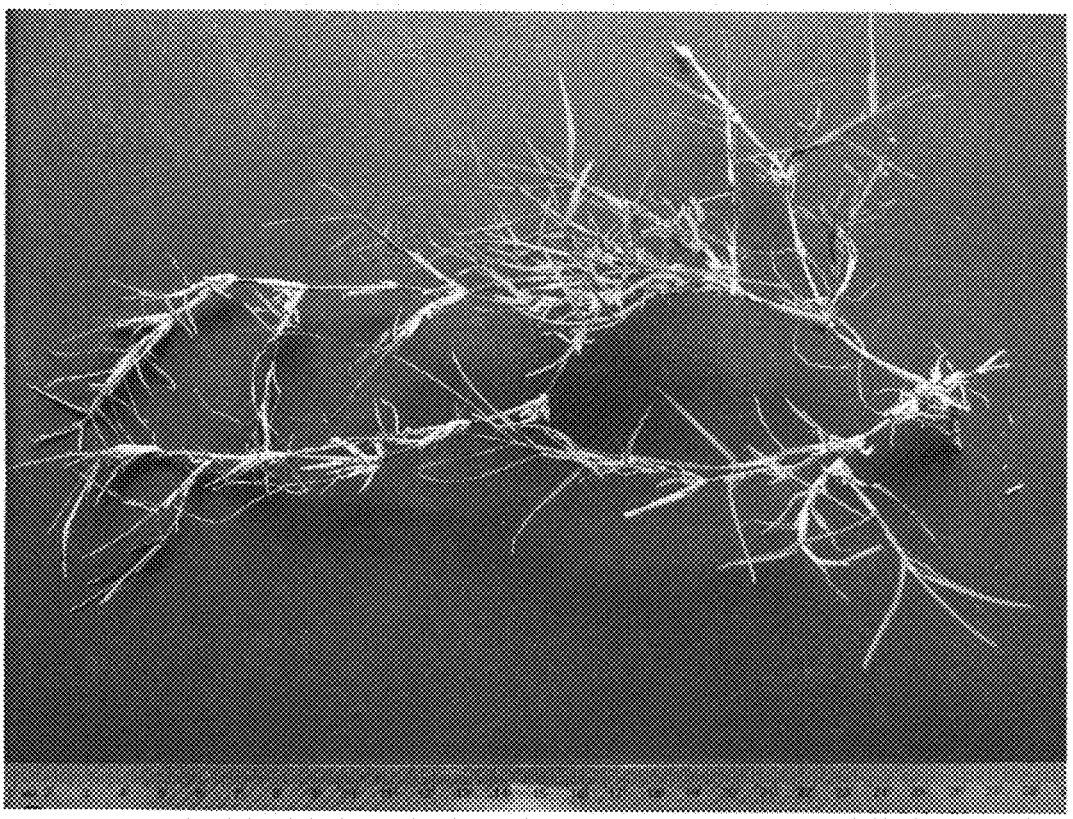
FIG. 2 shows an exemplary stolon as well as the foliage of 'CD08'.
Figure 3:
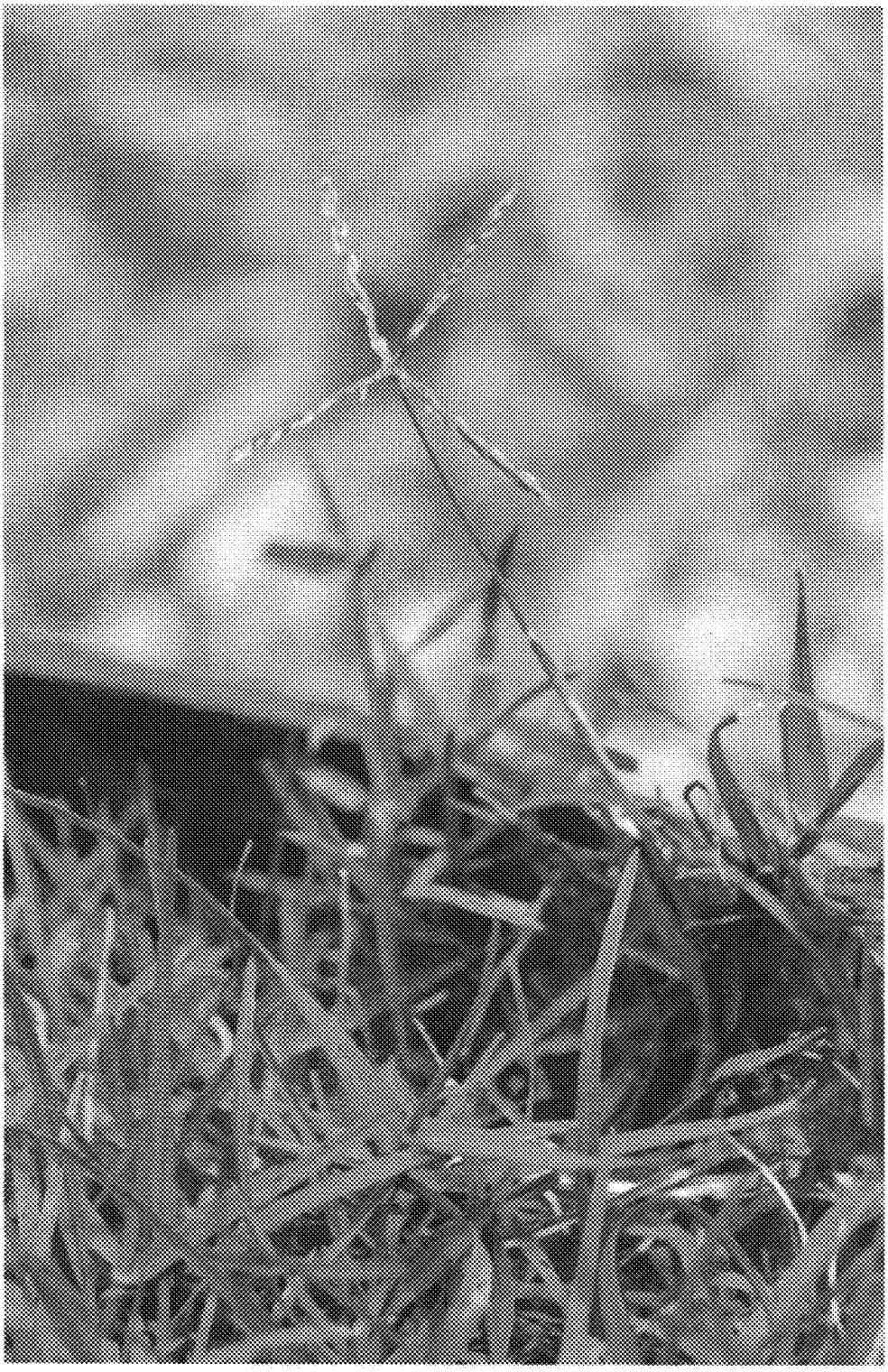
FIG. 3 shows an exemplary inflorescence of 'CD08'

The following is a detailed botanical description of a new and distinct variety of a *Cynodon dactylon* ornamental plant known as 'CD08'. Plant observations were made on plants grown in Awendaw, S.C. Unless indicated otherwise, the descriptions disclosed herein are based upon observations made in May 2015 of mature 'CD08' plants grown in a 3-gallon nursery pot in an outdoor growing area. Plants were grown for approximately 10 months, with two applications of a slow release granular fertilizer and overhead irrigation. Plants were trimmed 2 weeks before assessment. Those skilled in the art will appreciate that certain characteristics will vary with older or, conversely, younger plants. 'CD08' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light quality, light intensity, day length, cultural conditions and the like. Color notations are based on *The Royal Horticultural Society Color Chart,* of The Royal Horticultural Society, London, 1986 edition.

Technical Description of the Variety

Plant description:

- *Growth habit*.—Perennial plant with a prostrate growth habit forming a tight mat of stolons which root adventitiously on the ground surface and branch heavily at the stolon nodes. Culms are decumbent. Root system is typical for that of *Cynodon dactylon*; a network or rhizomes and fibrous feeder roots.
- *Height*.—Mature sward is approximately 6 cm from soil surface to the top of the grass canopy, although sward height will vary depending on the level of maintenance and cultural practices employed.
- *Growth rate*.—Vigorous.
- *Disease/pest resistance*.—Neither tolerance nor resistance to normal diseases and pests of *Cynodon dactylon* has been observed.
- *Temperature tolerance*.—*Cynodon dactylon* is known to tolerate temperatures from approximately 15 degrees Fahrenheit to at least 115 degrees Fahrenheit.
- *Drought tolerance*.—Like other *Cynodon dactylon*, 'CD08' exhibits good drought tolerance.
- *Soil tolerances*.—Tolerant of most soil types; from sandy loam to loamy clay.

Stolon:

- *General habit*.—Prostrate and highly branched; potentially branching at every node.
- *Stolon length*.—Longest observed stolon is 24 cm, although stolon length will vary depending on the level of maintenance and cultural practices employed.
- *Stolon width*.—Approximately 1.5 mm for the most mature stolons observed.
- *Stolon color* (*adaxial & abaxial surfaces*).—Generally, immature stolons are yellow-green 146B along the internode and near yellow-green 148A at and near the node and mature stolons are closest to greyed-orange 164C.
- *Stolon internode length*.—Varying from 22 to 38 mm, depending on the age of the stolon.

Foliage:

- *Attachment*.—Sessile to stolons.
- *Length of blade*.—Longest observed leaf blade measuring 41 mm.
- *Width of blade*.—2 mm, at the widest point of the leaf.
- *Shape*.—Linear.
- *Apex*.—Acute.
- *Leaf cross-section*.—Typically flattened; occasionally conduplicate.
- *Margin*.—Entire.
- *Texture* (*adaxial and abaxial surfaces*).—Glabrous.
- *Leaf color* (*adaxial & abaxial surfaces*).—Juvenile: Yellow-green 147B; mature: Yellow-green 147B.
- *Venation*.—Type — Parallel.
- *Venation color*.—Adaxial surface is yellow-green 147B and abaxial surface is yellow-green 147C.
- *Leaf sheath*.—Glabrous; ranging from 8 to 10 mm long. Color is near yellow-green 147A.
- *Collar*.—Approximately 1 mm long and constricted. Color approximates to yellow-green 145A to yellow-green 145B.
- *Ligule*.—Fringe of fine hairs, approximately 1.5 mm long.

Inflorescence:

- *Natural flowering season*.—Spring to fall; in Northern hemisphere, April to November.
- *Inflorescence type and habit*.—Digitate raceme, comprised of a short culm and typically with 4 terminal spikelets.
- *Quantity of inflorescences*.—Varies greatly depending on season and environmental factors; fewer than 5 observed.
- *Culm description*.—Culm attitude — Decumbent. Culm dimensions — Variable; longest culm observed measuring 45 mm long and approximately 0.75 mm wide. Culm color — Yellow-green RHS 146B to 146C.
- *Spikelet description*.—Quantity of spikelets per raceme — Three to four. Spikelet attitude — Decumbent to semi-erect. Spikelet dimensions — Variable, with the longest spikelet observed measuring 26 mm long and approximately 0.75 mm wide. Quantity of florets per spikelet — Approximately one floret for every 2.5 mm of spikelet. Floret — Lanceolate; apex is acute; approximately 2.0 to 2.5 mm long and 1 mm wide; color grayed yellow RHS 160D and fading to grayed white (near RHS 155D). Glumes — Absent. Awns — Absent. Rachilla — Approximately 2 mm in length; width is approximately 0.25 mm; color is yellow-green RHS 146B.

Reproductive organs:

- *Anthers*.—Color is grayed yellow RHS 160D, changing to grayed orange RHS 174A; length is approximately 1.25 mm and the observed width is 0.5 mm.
- *Stigma*.—Featherlike; length is approximately 1.5 mm; width is approximately 0.75 mm; color is red-purple 59B.

Seeds and fruits: Not observed.

Comparison of 'CD08' With the Parent

Plants of the new cultivar 'CD08' are similar to plants of the seed parent variety, 'WPG3', in many horticultural characteristics. However, 'CD08' exhibits a greater degree of stolon branching, shorter stolon internodes, a slightly broader leaf texture and a darker green foliage color when compared to the parent plant.

Comparison of 'CD08' With Other Varieties of *Cynodon Dactylon*

Plants of the new cultivar 'CD08' are similar to the commercial variety, 'Riley's Super Sport' (U.S. Plant Pat. No. 11,181), in many horticultural characteristics. However, 'CD08' exhibits a longer stolon internode length, a slightly lighter green foliage color, broader leaf blades, and fewer inflorescences.

That which is claimed:

1. A new and distinct cultivar of *Cynodon dactylon* plant named 'CD08', substantially as herein shown and described.

* * * * *